(12) United States Patent
Jang

(10) Patent No.: US 10,653,582 B2
(45) Date of Patent: May 19, 2020

(54) TOE CORRECTOR

(71) Applicant: Youn Jung Jang, Seoul (KR)

(72) Inventor: Youn Jung Jang, Seoul (KR)

( * ) Notice: Subject to any disclaimer, the term of this patent is extended or adjusted under 35 U.S.C. 154(b) by 368 days.

(21) Appl. No.: 15/482,901

(22) PCT Filed: Dec. 16, 2015

(86) PCT No.: PCT/KR2015/013809
§ 371 (c)(1),
(2) Date: Apr. 10, 2017

(87) PCT Pub. No.: WO2016/099152
PCT Pub. Date: Jun. 23, 2016

(65) Prior Publication Data
US 2017/0273866 A1  Sep. 28, 2017

(30) Foreign Application Priority Data

Dec. 18, 2014 (KR) .................. 20-2014-0009362 U

(51) Int. Cl.
A61H 39/06 (2006.01)
A61L 9/013 (2006.01)
(Continued)

(52) U.S. Cl.
CPC ............. *A61H 39/06* (2013.01); *A61F 5/019* (2013.01); *A61F 5/14* (2013.01); *A61H 1/008* (2013.01);
(Continued)

(58) Field of Classification Search
CPC ..... A61H 2205/12; A61H 39/06; A61F 5/019; A61F 5/014; A61F 5/0102; A61F 5/0118;
(Continued)

(56) References Cited

U.S. PATENT DOCUMENTS 1,245,253 A * 11/1917 Marglous ................ A61F 5/019
602/30
2,506,308 A * 5/1950 Maynier ................. A61F 5/019
602/30
(Continued)

FOREIGN PATENT DOCUMENTS

KR       200296822 Y1   12/2002
KR       200390011 Y1    7/2005
(Continued)

OTHER PUBLICATIONS

International Search Report for PCT/KR2015/013809; International Filing Date: Dec. 16, 2015; 2 pgs.

*Primary Examiner* — Bradley H Philips
*Assistant Examiner* — Vincent D Hoang
(74) *Attorney, Agent, or Firm* — Schmeiser, Olsen & Watts, LLP

(57) ABSTRACT

A toe corrector is provided including: a floor part; correction protrusions protruding between each toe from an upper surface of the floor part to correct the toes; a connection part for connecting the upper ends of the correction protrusions so that correction protrusions are put on toes to be fixed; and light emitting units for emitting light by independently generating electricity, which are provided inside the correction protrusions and on the floor part.

1 Claim, 3 Drawing Sheets

(51) Int. Cl.
- *A61F 5/01* (2006.01)
- *A61H 39/04* (2006.01)
- *A61F 5/14* (2006.01)
- *A61H 1/00* (2006.01)
- *A61L 9/01* (2006.01)

(52) U.S. Cl.
CPC ................ *A61H 39/04* (2013.01); *A61L 9/01* (2013.01); *A61L 9/013* (2013.01); *A61H 2205/12* (2013.01)

(58) Field of Classification Search
CPC ............ A61F 5/0127; A61F 2005/0158; A61F 5/013; A61F 5/05866; A61F 5/05875; A61F 2005/0155; A61L 9/01; A43B 7/145; A43B 7/26
USPC ...................................................... 601/15, 28
See application file for complete search history.

(56) References Cited

U.S. PATENT DOCUMENTS

| | | | | |
|---|---|---|---|---|
| 2,949,112 A | * | 8/1960 | Murray | A61F 5/019 602/30 |
| 3,943,922 A | * | 3/1976 | Umeda | A61F 5/019 602/31 |
| 4,558,694 A | * | 12/1985 | Barber | A61F 5/10 602/21 |
| 5,076,263 A | * | 12/1991 | Funatogawa | A61F 5/019 132/73 |
| 5,829,171 A | * | 11/1998 | Weber | A43B 7/025 36/93 |
| 7,131,939 B2 | * | 11/2006 | Ferri | A61F 5/10 482/148 |
| 2008/0113854 A1 | * | 5/2008 | Ferri | A61F 5/019 482/148 |
| 2011/0077570 A1 | * | 3/2011 | Findeisen | A61F 5/019 602/30 |
| 2013/0247424 A1 | * | 9/2013 | Tseng | A43B 3/0005 36/136 |
| 2015/0059214 A1 | * | 3/2015 | Donovan | A43B 1/0027 36/100 |
| 2015/0287904 A1 | * | 10/2015 | White | H01L 41/042 310/319 |

FOREIGN PATENT DOCUMENTS

| | | |
|---|---|---|
| KR | 10-2013-0014281 A | 7/2011 |
| KR | 101055859 B1 | 8/2011 |
| KR | 10-2014-0000558 A | 1/2014 |
| KR | 200477542 Y1 | 6/2015 |

* cited by examiner

TOE CORRECTOR

CROSS-REFERENCE TO RELATED APPLICATIONS

This application claims priority to PCT Application No. PCT/KR2015/013809, having a filing date of Dec. 16, 2015, based on KR 20 2014 0009362, having a filing date of Dec. 18, 2014, the entire contents of both are hereby incorporated by reference.

FIELD OF TECHNOLOGY

The following relates to a toe corrector, and more particularly, to a toe corrector which prevents hallux valgus in which toes are bent or deformation symptoms.

BACKGROUND

Recently, as an income level is improved, health awareness is raised, and especially, foot health is regarded and much research on feet has been conducted.

Acupuncture points connected to vital organs of a human body exist in feet, and especially, it is known that many acupuncture points exist in toes. Accordingly, many correctors, which are helpful for health by stimulating a sole and toes to stimulate acupuncture points, have been developed.

It is helpful for preventing amnesia, dementia, and palsy when a toe portion is stimulated, and a sole is helpful for shoulder discomfort, a heel portion of the sole is helpful for indigestion, diabetes, and constipation, and an upper rear portion of the heel is helpful for prevention treatments of menstrual irregularity, menstrual cramps, the prostate, nosebleeds, or the like.

However, as wearing of shoes having a narrow width, such as high heels, is increased, deformation symptoms, such as hallux valgus in which toes become freakish, corns, calluses, hammer toe, and the like, have occurred.

Due to these symptoms, a total weight of a body is concentrated on one part of the body, and thus the body not only is leaned toward one side of the body but also the backbone and legs are affected so that there is a problem in which discomfort, such as in the waist, sacrum, neck, a disk, a shoulder, stenosis, and chronic fatigue, is developed.

SUMMARY

An aspect relates to a toe corrector having correction protrusions inserted between adjacent toes formed to prevent hallux valgus in which toes are bent or deformation symptoms, which is capable of correcting with a correct gait using footsteps, thereby properly correcting a backbone and legs by dispersing a total weight of a body to five toes so that a body does not lean toward one side.

Technical Solution

One aspect of the present invention provides a toe corrector includes: a bottom part; correction protrusions protruding between adjacent toes from an upper surface of the bottom part to correct the toes; a connection part for connecting the upper ends of the correction protrusions so that correction protrusions are fitted on toes to be fixed; and light emitting units for emitting light by self-generating electricity, which is provided inside a correction protrusion and the bottom part, wherein the bottom part includes a pad provided inside the bottom part, a heating line arranged zigzag on one side surface of the pad, a power transmission portion connected at an end portion of the heating line and provided to be exposed to the outside of the bottom part for receiving power from the outside, and an acupressure portion for performing acupressure on skin by a plurality of protrusions formed on the upper surface of the bottom part in contact with a part of the skin between the sole and toes, wherein the correction protrusions include a first protrusion protruding between a big toe and a long toe, a second protrusion protruding between the long toe and a third toe, a third protrusion protruding between the third toe and a fourth toe, and a fourth protrusion protruding between the fourth toe and a little toe, wherein upper edges of the first protrusion to the fourth protrusion are formed as chamfers and the edges formed as chamfers are formed to be a round shape, sides of the first protrusion to the fourth protrusion in contact with sides of the toes are formed to be recessed toward the inside of the first protrusion to the fourth protrusion to cover the sides of the toes, wherein the connection part includes a first connecting bridge for connecting each of the upper ends of the second protrusion and the third protrusion, and a second connecting bridge for connecting each of the upper ends of the third protrusion and the fourth protrusion, wherein one end of the first connecting bridge is connected to a side surface of the second protrusion and the other end is coupled to the third protrusion while a first coupling protrusion inserted and coupled to a first recessed groove formed in an upper surface of the third protrusion is formed at the other end, wherein one end of the second connecting bridge is connected to a side surface of the third protrusion and the other end is coupled to the fourth protrusion while a second coupling protrusion inserted and coupled to a second recessed groove formed in an upper surface of the fourth protrusion is formed at the other end, wherein the light emitting unit includes a piezoelectric element provided inside the bottom part and a correction protrusion and configured to self-generate electricity when an external force is applied, a thin film battery which stores power generated from the piezoelectric element, and light emitting diodes (LEDs) provided on an upper surface of a correction protrusion for receiving the power stored in the thin film battery to emit light, and wherein the toe corrector further includes: a logo part bonded on the upper surface of a correction protrusion and a logo is printed on an upper surface thereof; and a fragrance emitting layer formed on the upper surface of a correction protrusion by applying a mixture in which a fragrance is added to a mixed UV coating agent consisting of an ultraviolet curable oligomer which widely influences physical properties to form a coating film for a surface of a photograph, an ultraviolet curable monomer, which is a diluent reacting with the oligomer, a photoinitiator which induces polymerization of the oligomer and the monomer, and an additive which is chemically combined with a coating film formed by the oligomer and the monomer to improve the durability or slipperiness of the surface of the photograph.

Advantageous Effects

Since a toe corrector according to embodiments of the present invention has correction protrusions inserted between adjacent toes formed to prevent hallux valgus in which toes are bent or deformation symptoms, a correct gait using footsteps can be corrected, thus a total weight of a body is dispersed to five toes, and a backbone and legs can be properly corrected so that a body does not lean toward one side.

BRIEF DESCRIPTION

Some of the embodiments will be described in detail, with reference to the following figures, wherein like designations denote like members, wherein.

DETAILED DESCRIPTION

Figure 1:
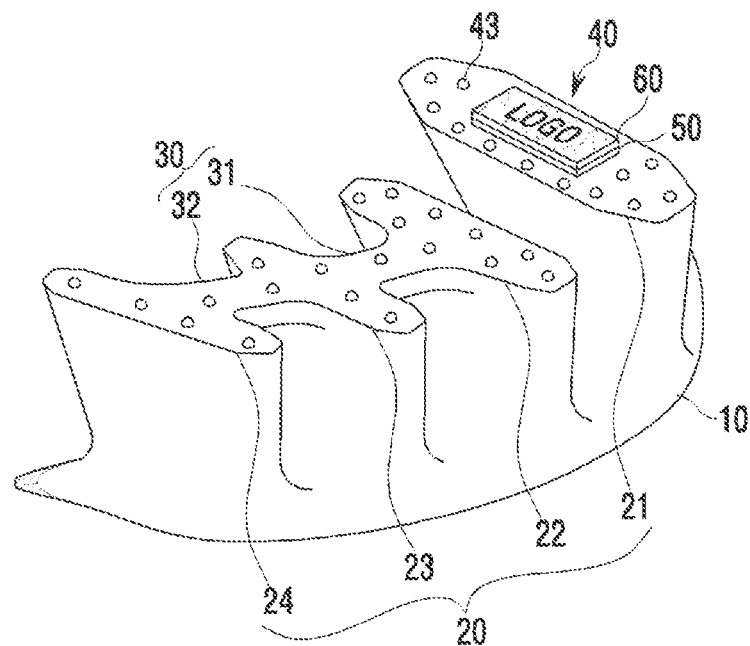
FIG. 1 is a perspective view illustrating a toe corrector according to an exemplary embodiment of the present invention.
Figure 2:
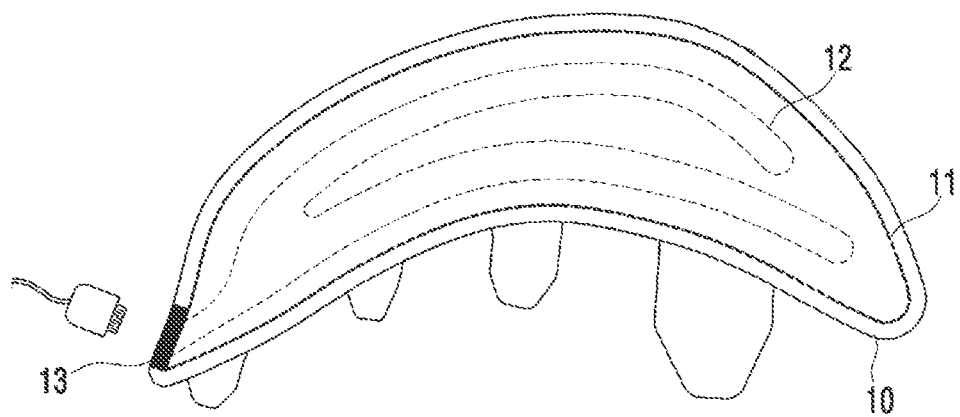
FIG. 2 is a bottom view illustrating the toe corrector according to the exemplary embodiment of the present invention.
Figure 3:
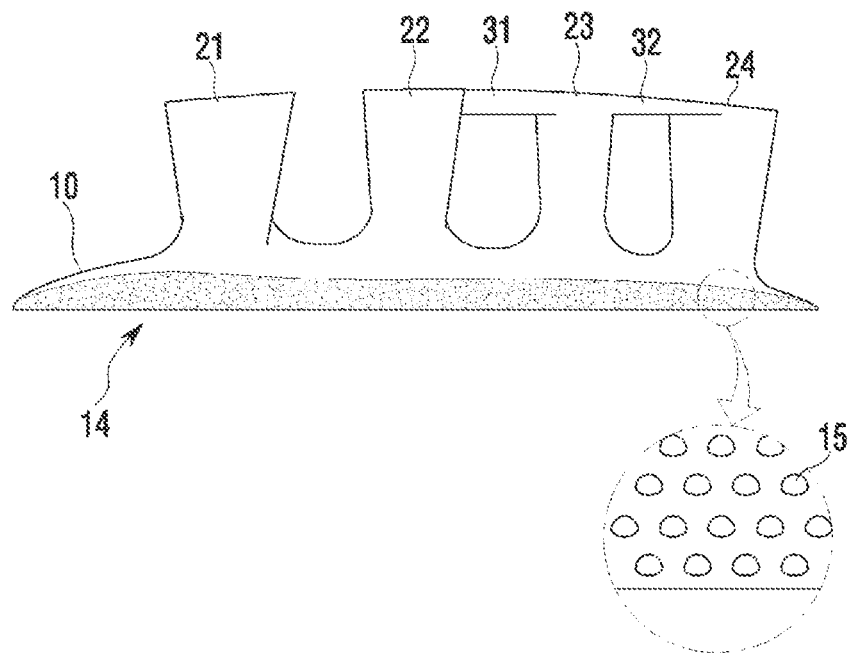
FIG. 3 is a rear view illustrating the toe corrector according to the exemplary embodiment of the present invention.
Figure 4:
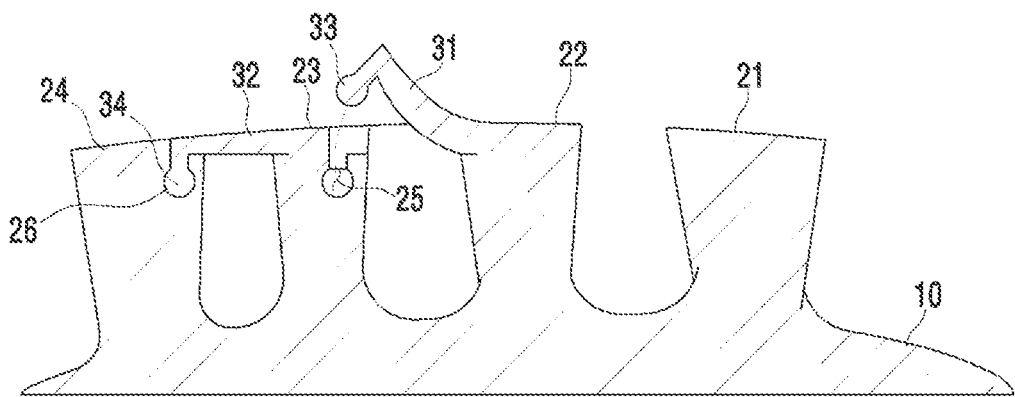
FIG. 4 is a front view illustrating the toe corrector according to the exemplary embodiment of the present invention.
Figure 5:
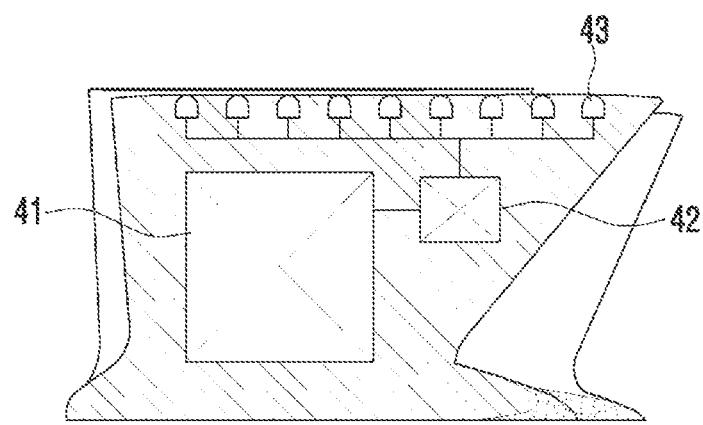
FIG. 5 is a side cross-sectional view illustrating the toe corrector according to the exemplary embodiment of the present invention.

Referring to FIGS. 1 to 5, the toe corrector according to embodiments of the present invention includes a bottom part 10, correction protrusions 20, a connection part 30, and light emitting units 40.

First, the bottom part 10 is supported by the ground and the correction protrusions 20 protrude from and are formed on an upper surface of the bottom part 10.

The bottom part 10 includes a pad 11, a heating line 12, a power transmission portion 13, and an acupressure portion 14.

The pad 11 is provided inside the bottom part 10.

The heating line 12 is arranged zigzag on one side surface of the pad 11.

The power transmission portion 13 is connected to an end portion of the heating line 12, is provided to be exposed to the outside of the bottom part 10, and receives power from the outside.

That is, heat is generated in the bottom part 10 by the power received from the outside, and thus a user's feet may be warmed due to the heat.

A plurality of protrusions 15 are formed on an upper surface of the bottom part 10 in contact with a part of the skin between the sole and toes so that the acupressure portion 14 performs acupressure on the skin.

Therefore, amnesia, dementia, palsy, and so on may be prevented.

The correction protrusions 20 protrude between adjacent toes from the upper surface of the bottom part 10, thereby correcting the toes.

The correction protrusions 20 include a first protrusion 21, a second protrusion 22, a third protrusion 23, and a fourth protrusion 24.

The first protrusion 21 is protruded between a big toe and a long toe.

The second protrusion 22 is protruded between the long toe and a third toe.

The third protrusion 23 is protruded between the third toe and a fourth toe.

The fourth protrusion 24 is protruded between the fourth toe and a little toe.

Upper edges of the first protrusion 21 to the fourth protrusion 24 are formed in chamfer shapes and the edges formed in the chamfer shapes are formed round.

Also, sides of the first protrusion 21 to the fourth protrusion 24 in contact with sides of the toes are formed to be recessed toward the inside of the first protrusion 21 to the fourth protrusion 24 to cover the sides of the toes.

The connection part 30 connects upper ends of the correction protrusions 20 so that the correction protrusions 20 are fitted on toes to be fixed.

The connection part 30 includes a first connecting bridge 31 and a second connecting bridge 32.

The first connecting bridge 31 connects the upper ends of the second protrusion 22 and the third protrusion 23.

Also, one end of the first connecting bridge 31 is connected to a side surface of the second protrusion 22, and the other end is connected to the third protrusion 23.

Here, a first coupling protrusion 33 inserted and coupled to a first recessed groove 25 formed in an upper surface of the third protrusion 23 is formed at the other end of the first connecting bridge 31.

The second connecting bridge 32 connects the upper ends of the third protrusion 23 and the fourth protrusion 24.

Also, one end of the second connecting bridge 32 is connected to a side surface of the third protrusion 23, and the other end is connected to the fourth protrusion 24.

Here, a second coupling protrusion 34 inserted and coupled to a second recessed groove 26 formed in an upper surface of the fourth protrusion 24 is formed at the other end of the second connecting bridge 32.

Accordingly, the toe corrector according to embodiments of the present invention can correct with a correct gait using footsteps, and thus a total weight of a body is dispersed to five toes so that the backbone and legs can be properly corrected so that a body does not lean toward one side.

The light emitting units 40 emit light by self-generating electricity, which are provided inside the bottom part 10 and the correction protrusions 20.

The light emitting unit 40 includes a piezoelectric element 41, a thin film battery 42, and light emitting diodes (LEDs) 43.

When an external force is applied to the piezoelectric element 41, the piezoelectric element 41 self-generates electricity, which is provided inside the bottom part 10 and the correction protrusions 20.

The piezoelectric element 41 is a semiconductor in which electric polarization occurs so that a potential difference is generated and a voltage is generated when an external force is applied thereto, and because such a technique is a well-known technique, detailed descriptions thereof will be omitted.

Power generated from the piezoelectric element 41 is stored in the thin film battery 42.

The LEDs 43 are provided on an upper surface of the correction protrusions 20, receive the power stored in the thin film battery, and thus emit light.

Here, it is preferable that the plurality of LEDs 43 be included.

Therefore, whenever the user walks or moves a toe, the piezoelectric element 41 generates power, the generated power is immediately stored in the thin film battery 42 to be supplied to the LEDs 43 in a constant voltage so that the light emitting units 40 emit light and cause a visual effect, and thus the toe corrector according to embodiments of the present invention can increase the promotion and usability of the product.

Meanwhile, the toe corrector according to embodiments of the present invention further includes a logo part 50 and a fragrance emitting layer 60.

The logo part 50 is bonded on the upper surface of the correction protrusion 20 and a logo is printed on an upper surface of the logo part 50.

The fragrance emitting layer 60 is formed on the upper surface of the correction protrusion 20 by applying a mixture in which a fragrance is added to a mixed UV coating agent consisting of an ultraviolet curable oligomer which widely influences physical properties to form a coating film for a surface of a photograph, an ultraviolet curable monomer which is a diluent reacting with the oligomer, a photoinitiator which induces polymerization of the oligomer and the monomer, and an additive which is chemically combined with a coating film formed by the oligomer and the monomer to improve the durability or slipperiness of the surface of the photograph.

That is, because a coating solution mixed with a natural fragrance or synthetic fragrance is applied on a surface of the printed logo, without performing an additional perfuming operation, an operation is simply and easily performed with only a process of applying a mixture, and thus the fragrance is emitted continuously from the logo for a long time so that the toe corrector according to the embodiment of the present invention emits a fragrance which may always provide fresh, comfortable and clean feeling to a user.

Also, it is preferable to selectively use a synthetic fragrance or natural fragrance which provides one fragrance among an apple fragrance, a strawberry fragrance, a grape fragrance, a vanilla fragrance, a quince fragrance, a jasmine fragrance, a rosemary fragrance, an acacia fragrance, an herbal fragrance, a freesia fragrance, a hazelnut fragrance, a mocha fragrance, a juniper fragrance, a lilac fragrance, and a lavender fragrance.

Meanwhile, the toe corrector according to the embodiment of the present invention further includes a timer (not shown) provided on the upper surface of the correction protrusion 20 and in which a battery is built in to operate the timer and time is displayed to check a wearing time, and a button (not shown) for turning on or off the timer and resetting the displayed time.

Here, when pushing the button to turn on the timer, the time starts to be checked, and it is also checked by adding onto the time checked when the timer is turned off. Also, when pushing the button for a predetermined time, the checked time is reset.

Therefore, the user can prevent excessive wearing and can be induced to wear steadily by checking the wearing time.

Although the present invention has been disclosed in the form of preferred embodiments and variations thereon, it will be understood that numerous additional modifications and variations could be made thereto without departing from the scope of the invention.

For the sake of clarity, it is to be understood that the use of 'a' or 'an' throughout this application does not exclude a plurality, and 'comprising' does not exclude other steps or elements.

The invention claimed is:

1. A toe corrector comprising:
   a bottom part;
   correction protrusions configured to protrude between adjacent toes from an upper surface of the bottom part to correct the toes;
   a connection part configured to connect upper ends of the correction protrusions so that correction protrusions are fitted on toes to be fixed; and
   light emitting units configured to emit light by self-generating electricity, which are provided inside the bottom part and the correction protrusions,
   wherein the bottom part includes:
   a pad provided inside the bottom part;
   a heating line arranged zigzag on one side surface of the pad;
   a power transmission portion configured to receive power from an outside so that the power transmission portion is connected to an end portion of the heating line and provided to be exposed to the outside of the bottom part and; and
   an acupressure portion configured to perform acupressure on skin by a plurality of protrusions formed on the upper surface of the bottom part in contact with a part of the skin between a sole and toes,
   wherein the correction protrusions include:
   a first protrusion configured to protrude between a big toe and a long toe;
   a second protrusion configured to protrude between the long toe and a third toe;
   a third protrusion configured to protrude between the third toe and a fourth toe; and
   a fourth protrusion configured to protrude between the fourth toe and a little toe,
   wherein upper edges of the first, second, third, and fourth protrusion are formed in chamfer shapes and edges formed in the chamfer shapes are formed round, sides of the first, second, third, and fourth protrusion in contact with sides of the toes are formed to be recessed toward an inside of the first, second, third, and fourth protrusion to cover the sides of the toes,
   wherein the connection part includes:
   a first connecting bridge configured to connect the upper ends of the second protrusion and the third protrusion; and
   a second connecting bridge configured to connect the upper ends of the third protrusion and the fourth protrusion,
   wherein one end of the first connecting bridge is connected to the second protrusion and the other end is connected to the third protrusion while a first coupling protrusion inserted and coupled to a first recessed groove formed in an upper surface of the third protrusion is formed at the other end, and
   wherein one end of the second connecting bridge is connected to the third protrusion and the other end is connected to the fourth protrusion while a second coupling protrusion inserted and coupled to a second recessed groove formed in an upper surface of the fourth protrusion is formed at the other end,
   wherein a light emitting unit of the light emitting units includes:
   a piezoelectric element provided inside the bottom part and the correction protrusions and configured to self-generate electricity when an external force is applied thereto;
   a thin film battery which stores power generated from the piezoelectric element; and
   a light emitting diode (LED) provided on an upper surface of the correction protrusions, configured to receive the power stored in the thin film battery, and configured to emit light, and
   wherein the toe corrector further includes:
   a logo part bonded on an upper surface of at least one of the correction protrusions and a logo is printed on an upper surface of the logo part; and a fragrance emitting layer formed on the upper surface of the correction protrusions by applying a mixture in which a fragrance is added to a mixed UV coating agent, the mixed UV coating agent comprising:

an ultraviolet curable oligomer which influences physical properties to form a coating film for a surface on the upper surface of the correction protrusions, an ultraviolet curable monomer which is a diluent reacting with the oligomer, a photoinitiator which induces polymerization of the oligomer and the monomer, and an additive which is chemically combined with a coating film formed by the oligomer and the monomer to improve durability or slipperiness of the surface on the upper surface of the correction protrusions.

* * * * *